US006262337B1

(12) United States Patent
von Euler et al.

(10) Patent No.: US 6,262,337 B1
(45) Date of Patent: Jul. 17, 2001

(54) TRANSGENIC ANIMAL WITH RECOMBINANT VASCULAR ENDOTHELIAL GROWTH FACTOR B (VEGF-B DNA) AND USES THEREOF

(75) Inventors: Gabriel von Euler, Stockholm; Karin Aase, Arsta; Christer Betsholtz, Frolunda; Ulf Eriksson, Balsta; Milos Pekny, Askim; Samuel Gebre-Medhin, Goteborg; Xuri Li, Solna, all of (SE)

(73) Assignee: Ludwig Institute for Cancer Research

( * ) Notice: Subject to any disclaimer, the term of this patent is extended or adjusted under 35 U.S.C. 154(b) by 0 days.

(21) Appl. No.: 09/025,701

(22) Filed: Feb. 18, 1998

Related U.S. Application Data
(60) Provisional application No. 60/038,202, filed on Feb. 18, 1997.

(51) Int. Cl.$^7$ .................................................. A01K 67/027
(52) U.S. Cl. .................................. 800/18; 800/3; 800/22; 800/25
(58) Field of Search ................................ 800/3, 8, 18, 21, 800/25, 24, 22; 435/325, 335, 354, 375; 424/93.21

(56) References Cited

U.S. PATENT DOCUMENTS
5,916,763 * 6/1999 Williams et al. .................... 435/69.1

OTHER PUBLICATIONS
Seamark, R.F. "Progress and Emerging Problems in Livestock Transgenesis: a Summary Perspective," Reprod. Fertil. Dev., vol. 6: 653–657, 1994.*

Mullins et al., "Perspective Series: Molecular Medicine in Genetically Engineered Animals," J. Clin. Invest., vol. 98, No. 11, Supplement, 1996.*

Moreadith et al., "Gene targeting in embryonic stem cells: the new physiology and metabolism," J. Mol. Med., vol. 75: 208–216, 1997.*

Olofsson et al. "Genomic organization of the mouse and human genes for vascular endothelial growth factor B (VEGF–B) and characterization of a second splice isoform," J. of Biological Chemistry, vol. 271, No. 32: 19310–19317, Aug. 1996.*

Olofsson et al. "Vascular endothelial growth factor B, a novel growth factor for endothelial cells," Proc. Natl. Acad. Sci., vol. 93, No. 6: 2576–2581, Mar. 1996.*

Zeng et al. "VEGF enhances pulmonary vasculogenesis and disrupts lung morphogenesis in vivo," Developmental Dynamics, vol. 211, No. 3: 215–227, Mar. 1998.*

Capecchi, M. R. "Targeted Gene Replacement," Scientific American, vol. 270, No. 3: 34–42, Mar. 1994.*

* cited by examiner

Primary Examiner—Karen M. Hauda
(74) Attorney, Agent, or Firm—Evenson, McKeown, Edwards & Lenahan, P.L.L.C.

(57) ABSTRACT

Transgenic animals containing recombinant DNA with modified nucleotide sequence from the vascular endothelial growth factor B (VEGF-B) gene, cells and methods for producing such animals, and methods of using them to assay substances for VEGF-B-like activity.

14 Claims, 6 Drawing Sheets

Fig. 1

1 kbp

RATIO; 1 : 2 : 1
GENOTYPING OF F₂ VEGF-B KNOCK OUT MICE BY PCR

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:1:

GTGAAGCTCC AGCCGAGCA                           19

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:2:

TAGTGTCTTC CATCTCTTT                                          19

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:3:

GCCCAGCTGT GTGACTGT                                           18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:4:

CCCACCCCAT GCTACACT                                           18

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:5:

TGTTCTCCTC TTCCTCATCT CC                                    22

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:6:

ATTGTCTGTT GTGCCCAGTC                                        20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

GCCATGTGTC ACCTTCGCAG                         20

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:8:

TGTCCCTGGA AGAACACAGC C                       21

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:9:

CGGGAAATCG TGCGTGACAT                         20

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:10:

GGAGTTGAAG GTAGTTTCGT G                       21

TRANSGENIC ANIMAL WITH RECOMBINANT VASCULAR ENDOTHELIAL GROWTH FACTOR B (VEGF-B DNA) AND USES THEREOF

This application claims priority to provisional application 60/038,202, filed in the United States of America, on Feb. 18, 1997.

FIELD OF THE INVENTION

This invention relates to a transgenic animal containing recombinant DNA having a modified nucleotide sequence from the vascular endothelial growth factor B (VEGF-B) gene and cells derived from the animal. The transgenic animal and cells are useful for research and development in the fields of angiogenesis and tumor development, and particularly for assaying substances for VEGF-B-like activity.

BACKGROUND OF THE INVENTION

Vascular endothelial growth factor (VEGF), as its name implies, is an endothelial cell-specific mitogen. It has potent angiogenic activity, that is, it promotes the growth of new blood vessels. A vital physiological process, angiogenesis implicates a number of proteins of the blood and of the cells in the blood vessels. During the angiogenic process, mitogenic factors, such as VEGF, play an important role. However, the biochemical details of the role these factors play have not always been forthcoming.

Since the identification and characterization of VEGF, a number of important findings have focused attention on the activity of angiogenic factors and the elucidation of new factors. The early findings showed that angiogenesis is required for normal development and physiology. Processes such as embryogenesis, wound healing, and corpus luteum formation, specifically, all involve angiogenesis and angiogenic factors. During wound healing, for example, VEGF mRNA levels increase suggesting a direct correlation between the expression of VEGF and the healing process. Also, a defect in VEGF regulation might be associated with wound healing disorders. (Frank, S., et al., J. Biol. Chem., 2705: 12607–12613 (1995).)

Other important findings related to angiogenic factors indicate that persistent and unregulated angiogenesis exacerbates and causes many diseases. For example, arthritis involves new capillaries invading the joint and destroying cartilage. In diabetes, new capillaries in the retina invade the vitreous humour, causing bleeding and blindness. (Folkman, J. and Shing, Y., J. Biol. Chem., 267(16): 10931–10934 (1992).) The role of angiogenic factors in these and other diseases has not yet been clearly established.

Another important finding involves the connection between angiogenesis and tumor development. Both tumor growth and metastasis are angiogenesis-dependent processes. (Folkman, J. and Shing, Y., J. Biol. Chem., 267(16): 10931–10934 (1992).) For example, when tumor cells are introduced into an animal, the expression pattern of VEGF mRNA reveals expression at the highest level in cells at the periphery of necrotic, tumor growth areas. Numerous blood vessels were identified within these areas. The expression of VEGF in these areas suggests that hypoxemia, a state of deficient oxygenation, triggers expression and release of VEGF in the necrotic tumor. The expression of another vascular endothelial cell mitogen, VEGF-B, discussed more fully below, has also been directly correlated with tumor growth, especially in melanomas. (U.S. application Ser. No. 08/609,443, filed Mar. 1, 1996.) VEGF is a member of a family of proteins structurally related to platelet-derived growth factor (PDGF). PDGF is a potent mitogen for smooth muscle cells, glial cells, and several other cell types. In one aspect, the members of the PDGF family are characterized by the presence of eight conserved cysteine residues. In their active, physiological state, the proteins are dimers formed by disulfide bonding, by both inter- and intramolecular bonds, at the eight cysteine residues. In another aspect, the family members are related in their mitogenic actions, especially on endothelial and related cell types.

Vascular endothelial growth factor B (VEGF-B), a non-glycosylated, highly basic growth factor, is a newly defined member of the PDGF family. With close structural similarities to VEGF, PDGF-A, PDGF-B, and PlGF (Placental Growth Factor), VEGF-B plays a role in vascularization of adult and embryonic tissues, and in muscle tissue in particular. VEGF-B acts also as a angiogenic mitogen. VEGF-B is expressed throughout many tissues in mammals but most abundantly in heart, skeletal muscle, and pancreas. The expression pattern of VEGF-B is different from that of VEGF, although both are expressed in many tissues. (Olofsson, B., et al., Proc. Natl. Acad. Sci. USA, 93:2576–2581 (1996).)

Like its related mitogenic proteins, VEGF-B exists as a disulfide bonded dimer in vivo. As a demonstration of the structural similarity, VEGF-B forms heterodimers with VEGF, consistent with the conservation of the eight cysteine residues involved in inter- and intramolecular disulfide bonding of PDGF-like proteins. Furthermore, the co-expression of VEGF-B and VEGF in many tissues suggests that VEGF-B-VEGF heterodimers occur naturally. VEGF also forms heterodimers with PlGF. (DiSalvo, et al, J. Biol. Chem. 270:7717–7723 (1995).) The production of heterodimeric complexes between the members of this family of growth factors could provide a basis for a diverse array of angiogenic or regulatory molecules.

As noted, VEGF-B is expressed in a number of tissues and cell types. For example, co-pending U.S. application Ser. No. 08/649,443, filed Mar. 1, 1996, specifically incorporated herein by reference, details RT-PCR assays demonstrating the presence of VEGF-B mRNA in melanoma, normal skin, and muscle. In addition, Northern blots show mRNA in a variety of mouse and human tissues, including heart, brain, and skeletal muscle.

Transgenic animal models are useful tools to study the functions and physiological activities of proteins, and a variety of such animals have been produced for this purpose. One particular technique for producing transgenic animals involves the process of homologous recombination. In homologous recombination, all or part of a genomic sequence is replaced with another DNA containing homologous sequences. Through transgenic manipulation and homologous recombination, a gene or part of a gene in the cells of an animal can be changed. Changing the gene to encode a protein that no longer functions as the native protein does creates a null mutant or null allele. (See, for example, U.S. Pat. No. 5,557,032.)

To study VEGF function and physiology, transgenic embryos containing a null mutant for the VEGF gene have been reported. (Carmetliet, P., et al., Nature, 380:435–439 (1996).) Some important findings resulted. The formation of blood vessels was abnormal, but not abolished, in embryos heterozygous for the VEGF null mutant. Embryos homozygous for the VEGF null mutant demonstrate an even greater impairment in angiogenesis. The homozygous embryos died in mid-gestation. Similar phenotypes were observed in heterozygous offspring embryos, generated by germ line transmission. However, since the Carmetliet et al. study was confined to embryos, no phenotype or use of animals was reported. Furthermore, the production of the VEGF transgenic embryos has not produced findings on the angiogenic properties or tumor growth modulating properties of all VEGF-like proteins.

Thus, despite the efforts of the art to elucidate the function and physiology of angiogenic factors, these factors are still incompletely understood, and there remains a need for means which can be used to evaluate the activities of angiogenic growth factors such as VEGF-B, as well as their roles in the various disease states discussed above, and/or which are useful to develop and/or evaluate other angiogenic peptides.

SUMMARY OF THE INVENTION

In one of its aspects, the invention involves production of transgenic animals that contain a mutated VEGF-B gene. The VEGF-B gene was mutated through a homologous recombination process. There are a number of uses for these transgenic animals. For example, study of the animals may provide important information on the therapeutic use and administration of VEGF-B polypeptides, fragments thereof, or analogs such as small molecules. In particular, the transgenic animals of the invention may be useful in elucidating the effects of VEGF-B and/or other cytokines on physiological phenomena such as permeability, inflammation and/or tissue repair. The animals or cells derived from the animals are useful in screening assays to identify angiogenic and/or tumor growth modulating compounds. The animals can also be used in methods to test VEGF-B agonists for in vivo distribution and function and non-toxicity and VEGF-B containing molecules.

In another aspect, the invention provides a method for producing a transgenic, non-human animal containing at least one non-functional mutated VEGF-B allele. The method comprises introducing a transgenic DNA into embryonic stem cells of a non-human animal, preferably a mouse. The transgenic DNA has a region homologous with a sequence of VEGF-B. Then, a cell is selected where the transgenic DNA has integrated into the genomic DNA of the stem cell at the site of at least one copy of an endogenous, genomic VEGF-B sequence. This cell is introduced into a blastocyst of a developing animal and allowed to develop into a transgenic animal.

In a further aspect, the invention provides animals produced from the method described above.

In yet another aspect, cells isolated from a transgenic animal produced by the above method are also provided.

The transgenic DNA used in any embodiment of the method of the invention comprises a sequence of nucleotides from the VEGF-B gene which has been changed, mutated, or modified in a number of ways known in the art. Thus, the DNA used to generate the transgenic animals can contain a number of different DNA sequences. The selection of an appropriate sequence depends on the desired effect. For example, at least one codon for cysteine can be changed or deleted. The resulting animal may produce a VEGF-B with an altered ability to form dimers with native VEGF-B or another PDGF-like protein. In a preferred embodiment, seven of the eight cysteine residues of VEGF-B have been deleted, resulting in a null mutant of VEGF-B.

In yet another aspect, the invention provides a method for screening compounds for the ability to effect angiogenesis or to modulate tumor growth or progression or to increase the musculature of the heart in a transgenic animal. The method comprises introducing the compound to a transgenic animal and detecting the vascular development in the animal. Alternatively, the method comprises introducing a tumor cell into a transgenic animal, introducing a compound into the same animal, and detecting the tumor development in the animal.

Numerous embodiments for the method described above are included within the scope of the invention. For example, a method for screening a compound for the ability to restore or detectably effect activity of the VEGF-B gene product comprising adding a compound to an appropriate cell line or introducing the compound into a transgenic animal can be devised. Transgenic animals and cell lines generated according to this invention can be used in these methods. Such animal or cell line systems can also be used to select compounds, which could be able to restore or to modulate the activity of the VEGF-B gene and/or angiogenesis. The compound may be in the form of a protein (recombinant or synthesized in vitro, for example) or in the form of DNA encoding VEGF-B or an analog of VEGF-B. This can be naked genomic DNA or cDNA operatively linked to a promoter, which could be further linked to a viral or bacterial vector. The DNA could be incorporated into a liposome structure, as exemplified in Lui et al., Nature Biotechnology, 15:167–172 (1997). The DNA or protein could also be provided to VEGF-B knock out mice embryos at the 8–16 cell embryonic stage.

The transgenic animals obtained with the mutant VEGF-B gene sequence (wildtype or mutated fragments thereof) can be used to generate double transgenic animals. For this purpose the mutant VEGF-B transgenic animal can be mated with other transgenic animals of the same species or with naturally occurring mutant animals of the same species. The resulting double transgenic animal, or cells derived from it, can be used in the same applications as the mutant parent transgenic animal.

Known methods to mutate or modify nucleic acid sequences can be used in conjunction with this invention to generate useful VEGF-B mutant animals, cell lines, or sequences. Such methods include, but are not limited to, point mutations, site-directed mutagenesis, deletion mutations, insertion mutations, mutations obtainable from homologous recombination, and mutations obtainable from chemical or radiation treatment of DNA or cells bearing the DNA. PCR analysis or DNA sequencing is used to determine the mutation generated if desired or necessary. The mutant animals, cell lines or sequences are then used in the DNA sequences, systems, assays, methods or processes described. The mutated or modified DNA will, by definition, be different, or not identical to the genomic DNA. Mutant animals are also created by mating a first transgenic animal containing the sequences described here or made available by this invention, with a second animal. The second animal can contain DNA that differs from the DNA contained in the first animal. In such a way, various lines of mutant animals can be created.

Furthermore, recombinant DNA techniques are available to mutate the DNA sequences described here, as above, link these DNA sequences to expression vectors, and express the VEGF-B protein or mutant. The VEGF-B mutant can thus be analyzed for biochemical or behavioral activity. In such a way, mutated DNA sequences can be generated that prevent the expression of an efficient VEGF-B.

Figure 1:
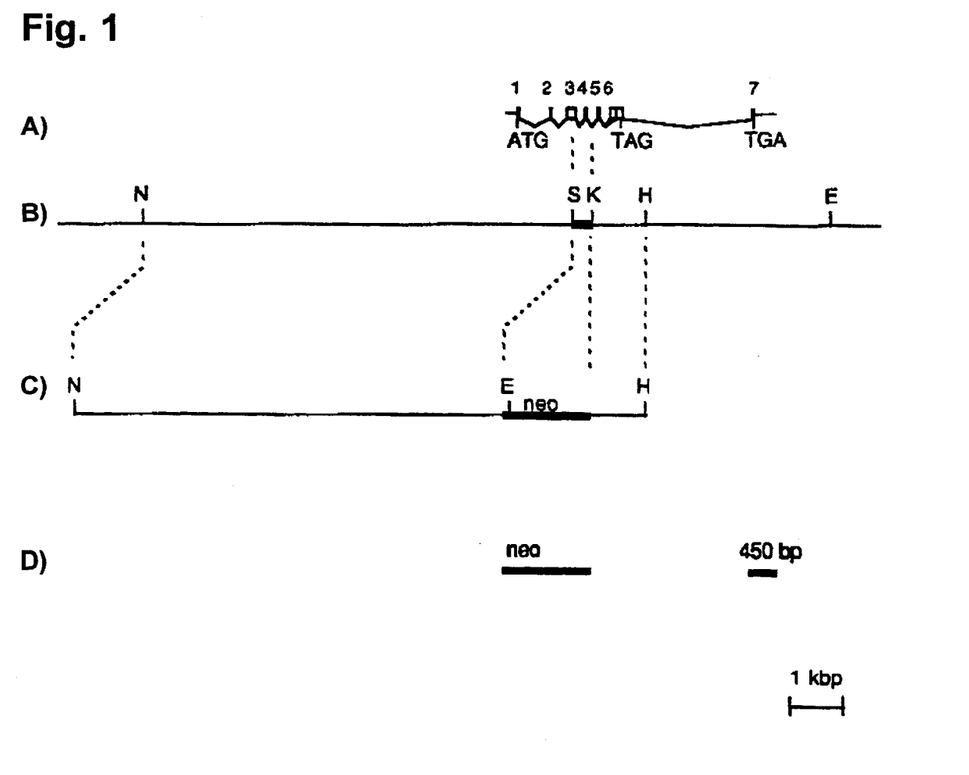
Figure 3:
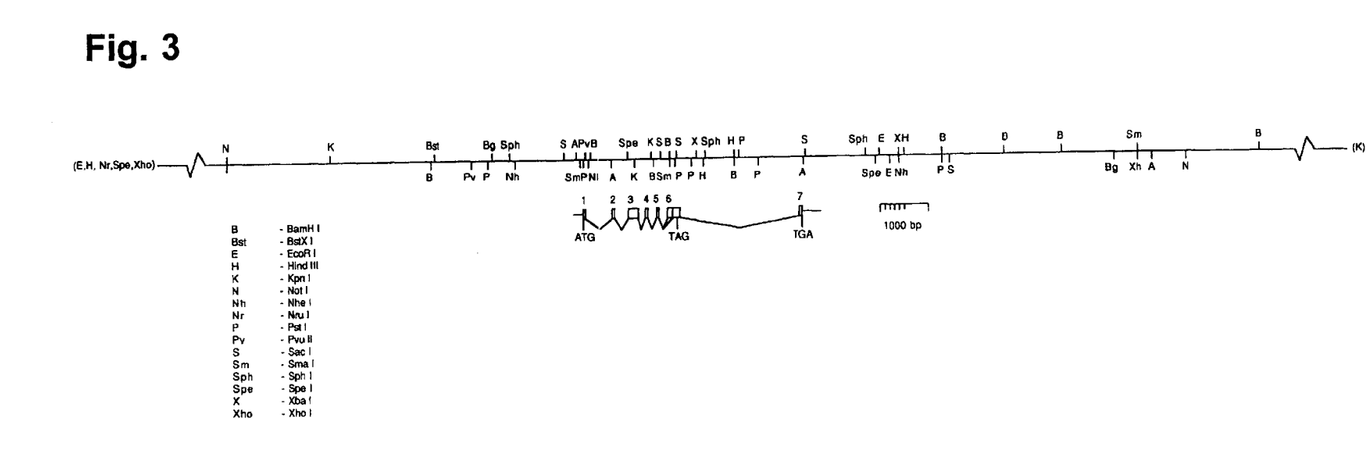
FIG. 3 shows a detailed restriction map of the mouse VEGF-B locus. Restriction enzymes and corresponding symbols are listed below.

The "modified VEGF-B DNA" of this invention refers to a sequence of nucleotides from the VEGF-B gene that has been modified by an in vitro or recombinant DNA technique. The modified VEGF-B DNA does not contain the exact sequence of nucleotides as the gene from the embryonic stem cells into which the transgenic DNA is to be introduced. However, modifications including deletions, substitutions, and insertions of nucleotides into the VEGF-B DNA sequence are specifically included. As an example, one particular modified VEGF-B DNA contains a deletion of part of exon three and all of exon 4 of the mouse VEGF-B DNA sequence. The restriction map of the VEGF-B locus (FIGS. 1 and 3) can be used to design numerous modified VEGF-B DNAs by deleting at least one restriction fragment.

The methods and transgenic animals of the invention provide useful models for deciphering the angiogenic and tumor growth modulating activity of various substances, including angiogenic growth factors such as VEGF-B. Therapeutic, diagnostic, and regulatory uses for VEGF-B can be determined from model systems employing the transgenic animals with altered VEGF-B genes. In particular, the transgenic animals according to the invention may be useful in the development of treatment protocols based upon the ability of VEGF-B to influence physiological phenomena such as permeability, inflammation and/or tissue repair. In addition, the methods and transgenic animals of the invention are useful to evaluate other polypeptides or small molecules for VEGF-B-like activity such as angiogenic activity or the activity that VEGF-B may have on endothelial cell gene expression which could affect their fundamental characteristics, e.g. the uptake of nutrients from the bloodstream to a particular tissue.

The transgenic animals of the invention may be used to elucidate the developmental and homeostatic functions of VEGF-B by monitoring and comparing the effects of different physiological stresses applied to wildtype (+/+), heterozygote (+/−) and null allele (−/−) animals. For example, the effects of VEGF-B on blood clotting times could be monitored through the use of wounding assays; the effects of VEGF-B on tumor growth could be determined by monitoring the proliferation of implanted tumor cells; the effects of VEGF-B on physical activity could be discovered by comparative physical activity studies, and/or the effects of VEGF-B on stress reactions could be determined through application of severe stresses such as exposure to compressed air. In addition, effects of VEGF-B on heart rate, cardiac output (e.g. blood pressure) and/or heamodynamic properties could be assayed by using the transgenic animals of the invention in procedures analogous to those described by Zhou et al., Nature Medicine, 4:201–14 (1998).

BRIEF DESCRIPTION OF THE DRAWINGS

The invention will be described in further detail hereinafter with reference to the accompanying drawings in which:

FIGS. 1A–D is a schematic representation of a strategy for producing a null mutation of the mouse VEGF-B gene;

FIGS. 4A–E shows a schematic drawing of the procedures used to generate a transgenic vector targeted for the mouse VEGF-B locus. Each of constructs A–E, described below, are shown in an exemplified method to generate a transgenic vector targeted to the mouse VEGF-B locus;

DETAILED DESCRIPTION OF ILLUSTRATIVE EMBODIMENTS

The descriptions and examples below are exemplary of the embodiments and scope of this invention. The invention is not limited to the scope of this description.

Persons skilled in the art will appreciate that the following examples and embodiments may be modified using techniques known in the art. For example, variations in the nucleic acid sequences described or claimed can be produced by known methods without altering the effects or advantages the inventors have shown. Such variations are therefore included within the scope of this description and invention.

In addition, detailed protocols for many of the techniques known in the art are described in Ausubel, F. M. et al. Eds. Current Protocols in Molecular Biology, Greene Publishing Associates and Wiley-Interscience, John Wiley & Sons, Boston, Mass. (1989), and Supplements through January 1997, hereinafter "Ausubel (1989)," as well as in Sambrook, J., et al., Molecular Cloning. A Laboratory Manual, 2nd Ed., Cold Spring Harbor Laboratory Press, Cold Spring Harbor, N.Y. (1989), hereinafter "Sambrook (1989)," and Manipulating the Mouse Embryo. A Laboratory Manual, edited by B. Hogan, R. Beddington, F. Constantini and E. Lacy, Cold Spring Harbor Laboratory Press, (1994), hereinafter "Hogan (1994)." These documents are specifically incorporated herein by reference. These documents may be relied on to enable one skilled in the art to practice the embodiments of the invention.

The phrases "null allele," "null mutation," and "null mutant" refer to gene sequences encoding an altered protein as compared to the wildtype protein. In general, the "null mutant" is altered in a manner resulting in a protein substantially incapable of its primary function. For example, a VEGF-B null mutant is a DNA sequence encoding a protein that no longer stimulates growth of vascular endothelial cells or which fails to exhibit any of the other effects of VEGF-B discussed above. However, structures related to other biochemical functions of VEGF-B, such as heparin binding and dimerization, may be present in the protein encoded by the null allele. In addition, the "null mutant" can refer to the animal or cell bearing a gene sequence of an altered protein, as discussed above.

Transgenic DNA refers to DNA that is capable of being introduced into a cell so that the DNA is incorporated into the genome of the cell. The cell may be capable of giving rise to a transgenic animal, which contains the transgenic DNA. Generally, the transgenic DNA is constructed as a vector, a transgenic vector, for administration into a particular cell. Such a vector need not be in a particular structural form, such as a circular form.

A recombinant gene or sequence simply means the gene or sequence has been manipulated in any one of a number of recombinant DNA techniques known in the art.

As used herein the term "modified VEGF-B DNA" refers to a VEGF-B nucleotide sequence from an animal which has been modified by one or more point mutations, site-directed mutagenesis, deletion mutations, insertion mutations, mutations obtainable from homologous recombination, and/or mutations obtainable from chemical or radiation treatment of DNA or cells bearing the DNA, or which is linked to another DNA sequence, such as a marker sequence, which is not associated with wildtype VEGF-B DNA in nature. The modified VEGF-B DNA may retain some or all of the activities of wild-type VEGF-B DNA, e.g. Flt-1 receptor binding motif.

The VEGF-B gene and DNA sequences referred to herein are not limited to genes or sequences from mouse or human. Any animal species can be used as a source of the VEGF-B gene. In the recombinant sequences incorporated into a transgenic DNA, the sequences homologous to the VEGF-B gene in a particular embryonic cell need not be from the same species as the embryonic cell.

The process for generating transgenic animals is essentially the same regardless of the species involved. Briefly, transfected cells are injected into embryos at a stage at which they are capable of integrating the transfected cells, for example, at the blastocyte stage. The embryo is then replanted into a surrogate mother, resulting in chimeric offspring possessing the transgenic DNA. Thus, all that is required is the appropriate embryonic stem cell from an animal.

The production of embryonic stem (ES) cells from a variety of animals is well known to those of ordinary skill in the art. Embryonic stem cells are available from a number of sources. These include mice, rats, cows, pigs, sheep, and other animals. For example, Joyner A. L., (1993), Gene Targeting. A practical approach, edited by Wood, R. and Hames, B. D., The Practical Approach Series, vol. 126, Oxford IRL Press (specifically incorporated herein by reference), describes methods of producing ES cells. Also, Manipulating the Mouse Embryo. A laboratory Manual, edited by B. Hogan, R. Beddington, F. Constantini and E. Lacy, Cold Spring Harbor Laboratory Press, (1994) describes manipulating the mouse embryo. In addition, Couly and Le Douarin, Development, 108:543–555 (1990), describes methods for isolating and manipulating chicken and quail embryos. Kimmel and Warga, Nature, 327:234–237 (1987), describe isolation and manipulation of zebrafish embryos. And Ware et al., "Development of Embryonic Stem Cell Lines from Farm Animals," Society for the Study of Reproduction, 38:241 (1988) discusses an embryonic stem cell culture condition amenable for many species like mouse, cattle, pig, and sheep. Accordingly, the invention is as applicable to other animals as it is to the specifically exemplified mice.

Various methods for inserting DNA into animal cells are known in the art. For example, transgenic DNA can be microinjected into appropriate cells. Viral vectors can be used to introduce the DNA into appropriate cells and the genome of those cells. (See, for example, Tsukui et al., Nature Biotechnology, 14:982–985 (1996).) And, cells can be manipulated in vitro through transfection and electroporation methods. (See Ausubel (1989) and Hogan (1994).)

Generally, transgenic DNA incorporates into a cell genome through either random integration or homologous recombination. Persons skilled in the art are familiar with strategies for increasing the relative frequency of homologous recombination versus random integration, in ES cells and other cells, in order to identify and isolate cells wherein homologous recombination has occurred. (See, Ausubel (1989), U.S. Pat. No. 5,557,032, and Hogan (1994), for example.) The design of transgenic DNA vectors may involve incorporating some portion of the cellular sequence into the transgenic DNA, or a sequence homologous to the cellular sequence. That portion must be sufficiently homologous to the cellular sequence to allow the transgenic DNA and the cellular DNA to hybridize in vivo, for homologous recombination to occur.

The transgenic DNA to be inserted into an embryonic stem cell in this invention, preferably comprises 5' and 3' regions of homology. These regions of homology function to allow the process of homologous recombination occur in the embryonic stem cell. Numerous publications, on which persons of skill in the art may rely, discuss how to construct regions of homology for use in homologous recombination. For example, Thomas & Capecchi, Cell, 51:503–512 (1987), Mansour et al., Nature, 317:348–352 (1988), and Capecchi, U.S. Pat. No. 5,487,992 each discuss strategies for designing regions of homology in a homologous recombination technique. Thus, methods for designing a sequence for homologous recombination are known in the art.

However, homologous recombination does not occur for each cell where the transgenic DNA has been introduced. In addition, it is often the case that more than one copy of the cellular DNA sequence desired to be changed or replaced through homologous recombination exists in the cell, such as in genes with more than one allele. Thus, through homologous recombination, some of the cells may incorporate the transgenic DNA at only one cellular sequence while other cells will incorporate the transgenic DNA into more than one cellular sequence, or even into every cellular sequence. Accordingly, both homozygous and heterozygous animals may be produced from the ES cells subjected to homologous recombination with the transgenic DNA. A homozygous animal may be mated with wildtype animals to produce further transgenic animals heterozygotic for the transgenic DNA.

EXAMPLES

To analyze the role of VEGF-B in development and maintenance of the vasculature in vivo, under both normal and diseased states, mice carrying mutant VEGF-B alleles were generated. One VEGF-B allele in the mice was functionally inactivated by the technique of homologous recombination. Mice generated from these cells, thus, carried one mutant and one wildtype VEGF-B allele.

FIG. 1 is composed of four subparts, 1A through 1D, and is a schematic representation of the strategy followed in producing a null mutation of the mouse VEGF-B gene. FIG. 1A is a schematic illustration of the exon-intron organization of the mouse VEGF-B gene. FIG. 1B is a restriction map of the VEGF-B locus in which the cleavage sites for a number of restriction enzymes are indicated. In the drawing the restriction enzymes are identified as follows: N=NotI; S=SpeI; K=KpnI; H=HindIII; and E=EcoRI. The SpeI-KpnI fragment, which is removed in an exemplified transgenic DNA construct described hereinafter, is indicated by the filled box. The transgenic DNA construct of FIG. 1C was used to generate a mutant VEGF-B allele. The construct contains a 5' homologous fragment (NotI/blunted SpeI) and a 3' homologous fragment (blunted KpnI/HindIII) of the VEGF-B gene, which flank the pPGK-neocassette (neo). FIG. 1D shows the locations of the DNA probes used to identify wildtype and mutant alleles of VEGF-B in Southern blot analysis.

Figure 2:
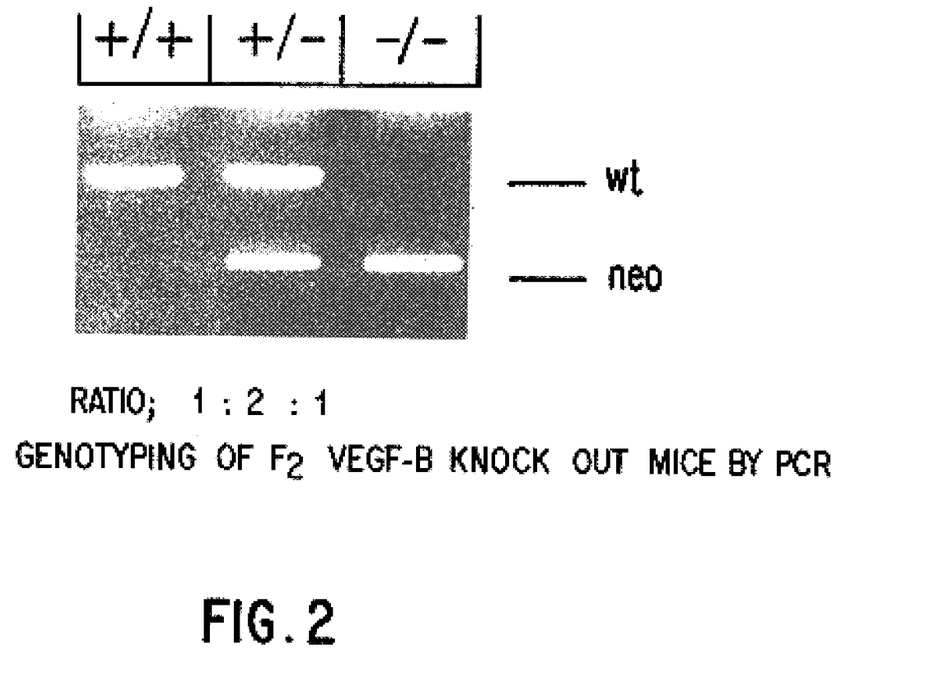
FIG. 2 shows agarose gel electrophoresis of PCR amplifications of tail DNA from the F2 generation of litter-mate homozygote VEGF-B (+/+), heterozygote (+/−) and homozygote knock out mice for the VEGF-B locus (−/−)

In FIG. 2, the migration of the amplified wildtype band (wt) and of the amplified band from the neomycin cassette (neo) are indicated to the right.

In the following sections, detailed procedures of how animals carrying mutant VEGF-B alleles were produced and the primary analysis of the resulting mouse phenotype are described.

EXAMPLE 1

Selection of VEGF-B Sequences Useful as Transgene

The DNA used to generate a transgenic animal can contain a number of different DNA sequences. The selection of an appropriate sequence depends on the desired effect. For example, if an animal possessing a null mutant of VEGF-B is desired, the transgenic DNA contains sequences encoding a protein that is incapable of VEGF-B primary function as a vascular endothelial cell mitogen. While assays to determine the mitogenic activity of a mutated protein may be used, structural information on the VEGF-B gene can also be used to accurately deduce the effect of a particular mutation scheme.

In this example, a portion of the VEGF-B mouse gene was deleted. The deleted portion contains seven of the eight cysteine residues important for disulfide bonding. As noted above, VEGF-B is a member of the PDGF family of growth factors. As the members of the family are structurally related, the effects of mutations on other PDGF family members can be extrapolated to indicate the effect on VEGF-B. Accordingly, a mutation in VEGF producing a particular effect can likely result in the same or similar effect in VEGF-B. Likewise, mutations in the other members of the PDGF family can be used to create mutations in the VEGF-B gene. This is especially the case where the structural information on all of the family members, or even with one other family member, indicates a conserved structure related to specific activity. With these considerations in mind, a null mutant was created wherein seven of the eight cysteine residues was deleted. Since the cysteine residues were known, from data on the PDGF family, to be involved in disulfide bonding and dimerization, a deletion of seven of the cysteines would predictably result in a nonfunctional, mutant VEGF-B protein. Further details on the selection of sequences in the transgenic DNA used for this invention follows.

In order to select the DNA sequences to be modified in the invention, the gene for mouse VEGF-B first was cloned from a mouse λFIXII-library (Stratagene; La Jolla, Calif.) using pcif-2 as the probe. The details of this procedure are described in Olofsson et al., J. Biol. Chem., 271:19310–19317 (1996) (specifically incorporated herein by reference). Three λ-clones denoted 10, 11 and 12, each carrying about 20 kb of mouse genomic DNA, were isolated and characterized. A detailed restriction map of the genomic DNA was generated by digestion of the λDNA with different restriction enzymes followed by identification of the restriction fragments by Southern blotting. Various $^{32}$p-labeled oligonucleotide probes obtained from the sequence of the mouse cDNA clones were used in the Southern blotting.

The information obtained from the restriction map of the λDNA harboring the VEGF-B gene was used to select a DNA for transgenesis. The DNA selected depends on the properties, characteristics, genotype, or phenotype the transgenic animal is to possess. Various properties, characteristics, genotypes, or phenotypes may be desired. For example, an animal where the VEGF-B DNA has been linked to a marker sequence, such as β-galactosidase, green fluorescent protein, or luciferase or the like known in the art, may be desired for assays to determine the localization of expressed VEGF-B protein. An animal with VEGF-B DNA operably linked to highly inducible promoter or promoter directing expression in mammary tissue may be desired for purposes of obtaining VEGF-B protein from the animal. Many promoters or expression systems that may be used are known in the art. In addition, mutant VEGF-B sequences, once operably inserted into a transgenic animal, may provide research animals for determining the molecular basis of angiogenesis or tumor development.

In one transgenic protocol, a null allele of the VEGF-B gene is desired. The gene product of the null allele would be non-functional with respect to the angiogenic properties of VEGF-B. Animals with a null allele of VEGF-B can be useful in a variety of assays to identify compounds that effect angiogenesis in an animal, for example.

One method for producing a null allele involves deleting or modifying the DNA sequence to prevent the formation of intramolecular or intermolecular disulfide bonds, or both. Specifically, regions encoding cysteine residues known to or believed to be involved in disulfide bonding are deleted. Alternatively, individual cysteine residues are mutated by a point mutation or site-directed mutagenesis procedure, many of which are known in the art. However, null alleles can be produced in a number of other ways. From the restriction map of VEGF-B, for example, convenient restriction sites can be selected for creating deletion mutants.

In principle, there are many ways of creating a null mutation, including, but not limited to: (i) deleting the entire gene; (ii) deleting a critical protein-coding sequence; and (iii) deleting a transcription regulatory sequence. Null mutations may also occur if the mutation affects splicing, mRNA stability, etc. Also, insertions or substitutions that alter the reading frame or introduce premature stop codons may cause null mutations.

From the restriction map shown in FIG. 1, one way of making a targeted, transgenic construct that would introduce a null mutation in the VEGF-B gene is by deleting a restriction fragment. Insertion of PTK neo into the "B" site in exon 1 likely creates a null mutation. From a more detailed restriction map, FIG. 3, other strategies may be devised. For example, deletions of any of exons 1, 2, 3, 4, or 5, and deletions of a combinations of more than one exon can also be devised.

Another method for producing a null mutant involves deleting those regions involved in receptor binding. For both PDGF and VEGF, structural information regarding receptor binding exists and is known in the art. That information can be used to delete related portions of the VEGF-B gene to create a null allele. Likewise, VEGF-B binding to receptor Flt-1 and methods for identifying VEGF-B analogs that bind to receptor Flt-1 are discussed in copending U.S. application Ser. No. 60/033,697, filed Dec. 21, 1996, specifically incorporated herein by reference. That information can be used to generate null alleles for VEGF-B as well.

From the discussion above, one skilled in the art will appreciate that a number of techniques known in the art can be used to design null alleles for VEGF-B. The invention, therefore, is not limited to the specifically exemplified deletion in generating a transgenic animal bearing a null allele of VEGF-B.

EXAMPLE 2

Production of Transgenic Vector with VEGF-B Deletion Mutant

In one embodiment of the invention, seven out of the eight cysteine residues in the amino terminal domain of VEGF-B were removed. This deletion disrupts three intramolecular disulfide bonds as well as two intermolecular disulfide bonds used for covalent dimerization of the mature VEGF-B molecule. To do this, a 330 bp SpeI-KpnI fragment was deleted. The fragment contains part of exon 3 and the whole of exon 4. Specifically, 33 amino acids encoded by the 3' part of exon 3 and all 24 amino acids of exon 4 were deleted. The generated VEGF-B protein from the targeted allele is non-functional as it lacks these critical amino acids and the allele is a null allele.

Figure 4:
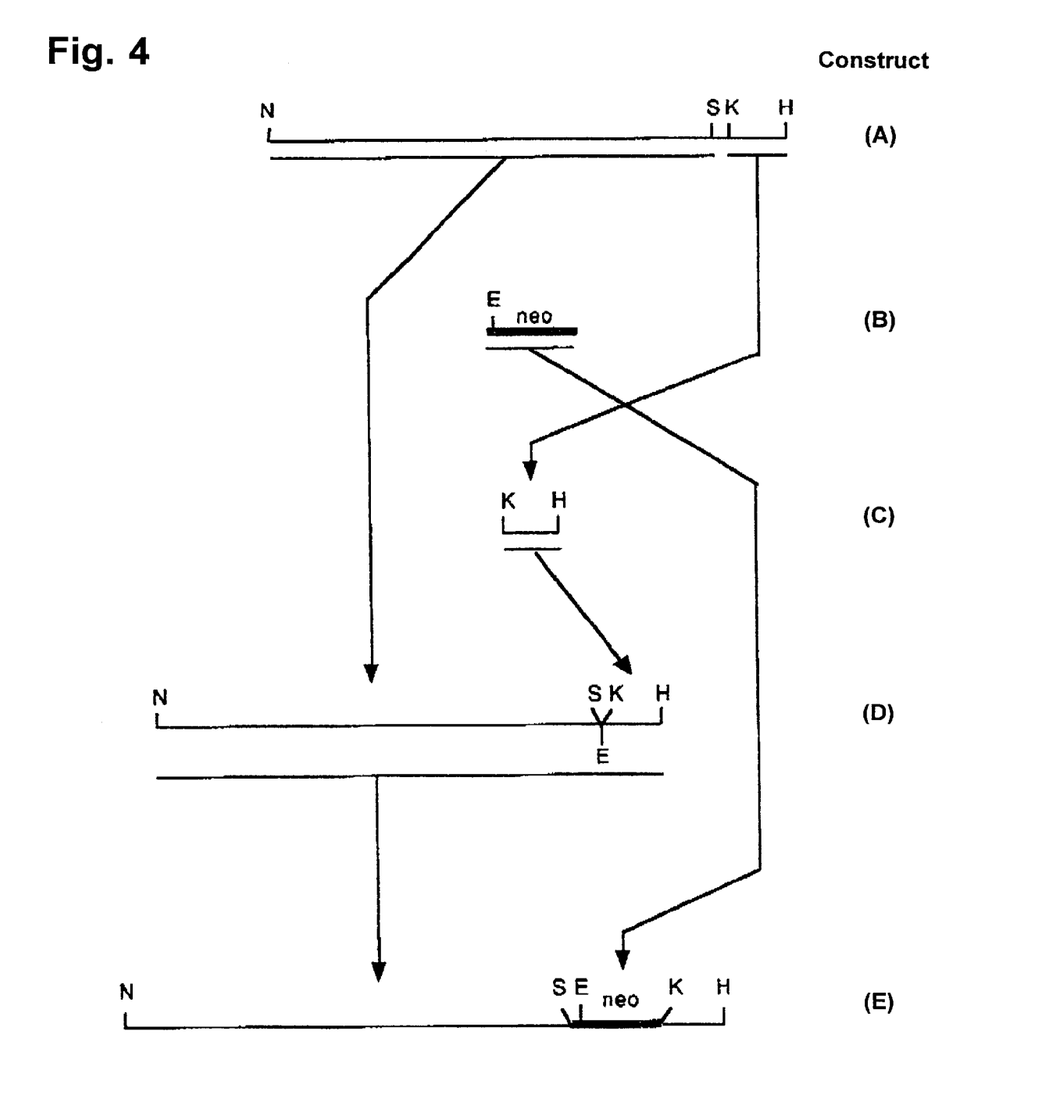

The starting materials for the generation of a recombinant transgenic vector lacking the SpeI/KpnI fragment of VEGF-B was a 10 kb NotI/HindIII fragment from λ-clone 10, subcloned into plasmid pBluescript™ (Stratagene) (construct A), and a 1.7 kb pPGK-neo cassette (Sibilia, M. Science 269:234–238 (1995)) cloned into pBluescript (construct B). A schematic of constructs A–E is found in FIG. 4.

The 1.2 kb KpnI/Hind III fragment used to generate the 3' region of the transgenic vector was isolated by digesting the 10 kb VEGF-B fragment from construct A with KpnI, generating blunt ends from the KpnI sticky ends with T4 polymerase, and finally cleaving with HindIII. This and all subsequent fragments were isolated on low gelling temperature (LGT) agarose gels made in 1×TBE (Tris Borate EDTA) buffer. The isolated 1.2 kb fragment was then ligated into EcoRV and HindIII digested pBluescript vector, resulting in construct C.

The 5' fragment of the transgenic vector was isolated from construct A by cleaving with NotI/SpeI. The isolated fragment was then ligated into NotI/SpeI digested construct C to generate construct D.

The pPGK-neo cassette was isolated by digesting construct B with NotI/HindIII and generating blunt ends with Klenow fragment. The resulting fragment was gel purified and then ligated into construct D digested with EcoRI and blunted with the Klenow fragment, resulting in construct E. This 11.2 kb vector with the pPGK-neo cassette inserted in the forward direction was chosen as the targeting vector for transgenesis.

A Southern blot assay was used to confirm the identity of wildtype versus mutated alleles. Genomic DNA was digested with EcoRI and prepared for blotting. The 450 bp radiolabeled fragment, used as the probe in the screening procedure above, mainly encompassed sequences encoding exon 7 and the 3' non-translated region of the VEGF-B cDNA. This probe was generated by PCR using DNA from clone 10 as the template. The primers used in the PCR application were 5'-GTGAAGCTCCAGCCGAGCA (sense-strand) (SEQ ID NO: 1) and 5'-TAGTGTCTTCCATCTCTTT (antisense-strand) (SEQ ID NO: 2). The mutant allele generated a genomic EcoRI restriction fragment of 6.5 kb while the wild-type allele generated a >20 kb fragment under these conditions.

EXAMPLE 3

Insertion of the Transgenic Vector Into Animal Cells

The vector containing the mutant VEGF-B (construct E) was transfected into E14.1 cells derived from the 129/SW mouse (Kuhn, R. et al., Science 254: 707–710 (1991)) by electroporation. Neomycin resistant clones were isolated by standard procedures and characterized. Manipulating the Mouse Embryo. A laboratory Manual edited by B. Hogan, R. Beddington, F. Constantini and E. Lacy, Cold Spring Harbor Laboratory Press, (1994) describes procedures for isolating and manipulating embryos (specifically incorporated herein by reference). Genomic DNA from several hundred clones were isolated, EcoRI digested, and analyzed by Southern blotting. Using these procedures, three positive clones denoted 1a, 8f, and 9h, were identified by detecting the 6.5 kb band and also the wild-type 20 kb band. Probing a Southern blot with radiolabeled PKG-neo cassette also gave the expected 6.5 kb band for clones 1a and 9h. These data show that one allele of the two VEGF-B alleles in the ES cells has been correctly targeted by the construct and that ES cells containing the null allele for VEGF-B were generated.

EXAMPLE 4

Production of Transgenic Animals

Cells from the cell line 9h were injected into mouse blastocysts using standard procedures. Manipulating the Mouse Embryo. A laboratory Manual, edited by B. Hogan, R. Beddington, F. Constantini and E. Lacy, Cold Spring Harbor Laboratory Press, (1994) describes procedures for injecting cells (specifically incorporated herein by reference). The blastocysts were implanted into pseudopregnant foster mothers. The resulting chimeric mice which were generated, i.e. those possessing the transgenic DNA, were identified by the coat color in the offspring.

For example, since the ES cells were derived from the 129/SW mouse with a chincilla (white-yellow) fur coat and carriers of the Agouti locus, whereas the host blastocysts were derived from the C57B1/6 mouse with a black coat and lacking the Agouti locus, the chimera will be a mixture of Chincilla (patches of skin to which only ES cells contributed), black (patches to which only host cells contributed) and brown or Agouti (patches of skin in which there was a mixture of 129/SW and C57B1/6 cells). The chimeric animals are brown because the Agouti protein secreted from 129/SW cells will stimulate C57B1/6 hair follicle cells to process the melanin (black pigment) in such a way that the hair becomes brown.

Male chimeric mice were mated with C57B1/6 wildtype females. The presence of brown mice in the offspring from these female mice indicated germline transmission of the transgenic DNA.

DNA prepared from the tails of these F1 mice were analyzed by Southern blotting as above. Generally, 0.5 cm of tail tissue was surgically removed and used to prepare DNA samples. The 6.5 kb EcoR1 fragment was present in 50% of the brown mice indicating that there was no selection against the targeted null allele of VEGF-B. The F1 mice carrying the targeted VEGF-B locus are heterozygotes as they also carry a wildtype allele for VEGF-B. The presence of normally developed F1 mice carrying one inactivated allele of VEGF-B show that gene dosage for VEGF-B is not critical for survival.

Heterozygote F1 mice were crossed and tail DNA from the offspring was analyzed by Southern blotting and by PCR. The results obtained using the two techniques were identical and the details of the PCR genotyping procedure is given. The PCR amplifications were performed using standard conditions with tail DNA from the F2 offspring as the template. The wildtype allele was identified as a 316 bp amplified band using two primers located in exon 3 and exon 4. These primers were 5'-GCCCAGCTGTGTGACTGT (forward) (SEQ ID NO: 3) and 5'-CCCACCCCATGCTACACT (reverse) (SEQ ID NO: 4), respectively. The targeted allele was identified as a 140 bp band using two primers located in the neomycin resistance gene. These primers were 5'-TGTTCTCCTCTTCCTCATCTCC (forward) (SEQ ID NO: 5) and 5'-ATTGTCTGTTGTGCCCAGTC (reverse) (SEQ ID NO: 6), respectively. The results from the PCR amplifications are summarized in FIG. 2. The analyses showed that mice homozygous for the targeted allele of VEGF-B are viable and analysis of a large number of animals of the F2 generation gave a 1:2:1 ratio of wildtype, heterozygotes, and homozygote animals carrying the null allele. Thus the null allele is inherited in a classical Mendelian fashion.

A first external inspection of adult knock out mice for VEGF-B did not reveal any gross morphological changes compared to wildtype mice. However, it was observed that the heart of some of the transgenic VEGF-B mutant mice appeared to be malformed. The hearts were generally smaller in size than wild-type and the larger vessels appeared more dilated. These phenotypes indicate that the VEGF-B knock out mice could be used as models to screen compounds for an effect on heart tissue growth or development.

EXAMPLE 5

Detection of VEGF-B Nucleic Acids in Cell or Tissue Specimens

Cell or tissue specimens can be obtained by many convenient methods known in the art. Generally, centrifuged cell pellets or tissue samples are immediately frozen. Total RNA is isolated by the guanidinium isothiocyanate procedure [Chomczynski et al., Anal. Biochem., 162:156–159 (1987)]. cDNA is synthesized using 0.2 µg of random hexadeoxynucleotide primers, 5 units of murine reverse transcriptase, 5 µg of total RNA as a template and a first-strand cDNA synthesis kit (Pharmacia). After incubation at 37° C. for 1 hour, the reaction mixture was stored at −70° C. Negative control samples for PCR amplification were prepared similarly except that reverse transcriptase was not added. β-actin also was tested as an internal standard because it is expressed at a constitutive high level, and its expression does not show much variation in different cells.

For PCR amplification, the primer sequences are selected from the VEGF-B and β-actin genes as follows: VEGF-B sense: 5'-GCCATGTGTCACCTTCGCAG-3' (SEQ ID NO: 7) VEGF-B antisense: 5'-TGTCCCTGGAAGAACACAGCC-3' (SEQ ID NO: 8) β-actin sense: 5'-CGGGAAATCGTGCGTGACAT-3' (SEQ ID NO: 9) β-actin antisense: 5'-GGAGTTGAAGGTAGTTTCGTG-3' (SEQ ID NO: 10) [β-actin sequences comprise nucleotides 2105–2125 and 2411–2432 from Ng et al., Mol. Cell Biol., 5:2720–732 (1985)]. An aliquot of 4 µl from the cDNA reaction product is heated to 94° C. for 5 minutes and used as a template for PCR amplification with 20 pmole of primers, 10×PCR buffer, 1 µl of 20 mM dNTPs and 2.5 U of Taq polymerase. Final volume is adjusted to 100 µl with DEPC treated water. Denaturation is at 95° C. for 1 minute, annealing at 62° C. for 45 seconds, and polymerization at 72° C. for 50 seconds, for a total of 35 cycles for VEGF-B and 25 cycles for β-actin. After every 5 cycles, 15 µl aliquots are taken for analysis.

Electrophoresis of 5 µl of the PCR reaction mix was performed in a 2% agarose gel containing ethidium bromide. The size marker DNA fragments ranged in length from 24 to 726 base pairs (ΦX174 DNA/Hinf I marker from Promega, Madison, Wis., USA).

EXAMPLE 6

Use of Cells and Tissue from Transgenic Animals

As noted above, the hearts of VEGF-B knock out mice appear smaller than wild-type, suggesting, inter alia, a usefulness in heart cell growth assays, heart rate assays, cardiac output assays or assays of other heamodynamic properties. Other uses in screening assays will be appreciated by one skilled in the art.

In order to use the cells and tissue of transgenic animals in such screening methods, cultures of the cells or tissue from transgenic animals can be used that contain at least one cell derived from the transgenic animal. The cells are grown as explants or separated by mechanical dispersion and grown as primary cultures. Alternatively, the cells are transformed into cell lines by transformation methods known in the art or by initially crossing the transgenic mouse with, for example, the H-2KtsA58 Mouse described by Jat et al. PNAS USA 88: 5096–5100 (1991), or other related methods known in the art (see, for example, McClean, J. S., Tibtech 11:232 (1993). In this way, the cross of the knock out mutant with the H-2K$^b$tsA58 transgenic mouse would generate conditionally immortal lines of various cells. Specifically, cells are initially grown at the permissive temperature for the ts (temperature sensitive) A58 T-antigen so that the cells can be cultured for many passages. The T-Ag immortalizes the cells. When the cells are shifted to the non-permissive temperature to disable the activity of the T-Ag, the cells differentiate, thereby potentially generating many different cell lines from different tissues.

EXAMPLE 7

Assays for Angiogenicity and/or Tumor Growth Modulating Activity

A tissue sample, such as heart explants from the VEGF-B knock out mice, which would also contain the responding cells, can be used to test VEGF-B analogs. The tissue sample or an explant is maintained in a solution as known in the art. Compounds, such as VEGF-B analogs or small molecules, are added to the tissue sample or explant and the effect on the tissue sample or explant analyzed. In this way, physiological effects such as angiogenicity, inhibiting or facilitating tumor growth, increase in musculature, or other effects associated with VEGF-B can be assayed for. One skilled in the art can rely on methods known in the art, such as those in Ausubel (1989) and Hogan (1994) for example, to devise particular embodiments.

EXAMPLE 8

Investigation of Expression of VEGF-B Transcripts

The expression of VEGF-B transcripts in heart and skeletal muscle was investigated by Northern blotting in wild-type mice (+/+), heterozygote mice (+/−) and in the homozygous knockout mice (−/−). VEGF-B deficient and wild type C57B1/6 mice were killed and different tissues were snap frozen and stored in −80° C. until used. Total cellular RNA were prepared using the guanidinium thiocyanate/acid phenol method [see Chomczynski et al., Analytical Biochemistry, 162:156–159 (1987)]. 20 µg of RNA from each sample was used per lane in a 1% agarose gel, running at 80 V for about 3 hours. The gel was subsequently transferred to a nylon membrane (Hybond™-N+, Amersham) followed by UV cross linking. Prehybridization was carried out for 2 hours in 5×SSC, 5×Denhardt solution, 0.5% SDS and 100 µg/ml of single-stranded DNA, followed by hybridization overnight with specific probes at 65° C. according to the manufacturer's protocol (Amersham).

The two probes used were (a) the full length mouse VEGF-B cDNA and (b) a probe covering the deleted portion of the VEGF-B gene in the null allele. A 1.8 kb VEGF-B$_{167}$ cDNA fragment was used to make the first probe using a random labelling kit (Amersham) following the recommended protocol. The second probe used in the Northern analysis was produced using a 148 bp fragment within the exons 3 and 4 of VEGF-B, which is replaced by the Neo gene in the null allele/targeting vector, and was labelled by a PCR method [see Konat et al., PCR Technology, pp. 37–42, Griffin eds., CRC Press, Boca Raton (1994)]. Taq DNA polymerase and $^{32}$p-dCTP were used in the labelling PCR with 30 cycles of 1 min at 94° C., 2 min at 58° C. and 3 min at 72° C.

Figure 5A:
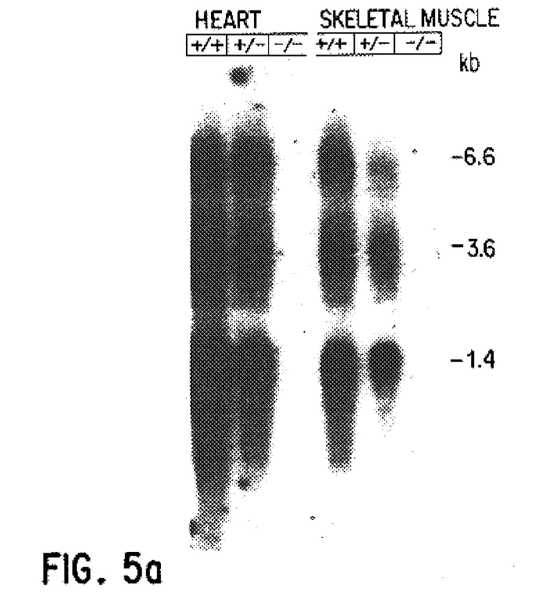
FIGS. 5a and 5b are Northern blots of RNA from heart and skeletal muscle tissues of wild type (+/+), heterozygote (+/−) and knock-out (−/−) mice.
Figure 5B:
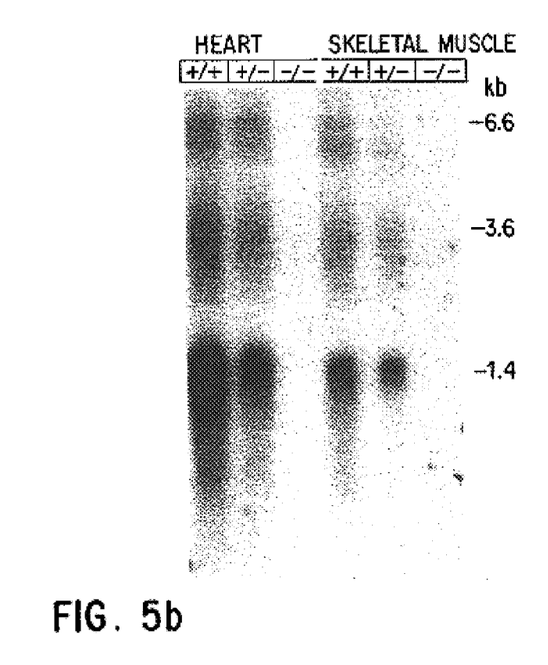

After wash, the membranes were exposed to X-ray films for 2 to 6 days. Membranes were stripped in boiling 0.5% SDS and exposed to phosphor Imager overnight to insure the complete stripping. FIG. 5a shows the results from the Northern blot using the full length mouse VEGF-B cDNA probe. FIG. 5b shows the results from a probe covering the deleted portion of the VEGF-B in the null allele.

The results show that both probes hybridize to the abundant 1.4 kb VEGF-B mRNA obtained from the +/+ mice and that two additional transcripts of lower abundance were also detected. The two minor transcripts were 3.0 and 6 kb in length, respectively. A clear reduction of the hybridization signal was obtained in the +/− mice, while both probes failed to detect any VEGF-B transcripts in the RNA samples obtained from the −/− mice. This shows that the targeted VEGF-B allele has been knocked out and resulted in a null allele, and that the −/− mice will have no synthesis of VEGF-B protein. The reduced levels of VEGF-B transcripts in the heterozygote also show that transcription of the remaining intact VEGF-B allele is not compensatorily upregulated.

EXAMPLE 9

Transplantation and Measurement of Tumors

As tumor growth and metastasis formation is known to depend on the neovascularization of the tumor tissue, the growth of a transplanted tumor was investigated in litter-mate wild-type (+/+) and VEGF-B deficient (−/−) mice. Male VEGF-B deficient (−/−) and litter-mate homozygous C57B1/6 mice (+/+) were used in the test. Mouse T241 fibrosarcoma cells were injected intradermally. The 6 to 8 weeks old mice were anesthetized by methoxyflurane before implantation of the tumor cells. Then 1×10$^6$ T241 mouse fibrosarcoma cells growing in log phase were suspended in 100 μliter of PBS, and implanted subcutaneously in the midline dorsum of each mouse. The growth of the tumor was measured in each of the animals. Tumors were observed and measured every other day using a caliper. Tumor volume was calculated using the formula: width$^2$×length×0.52 [see Boehm et al., Nature, 390:404–407 (1997)].

Figure 6:
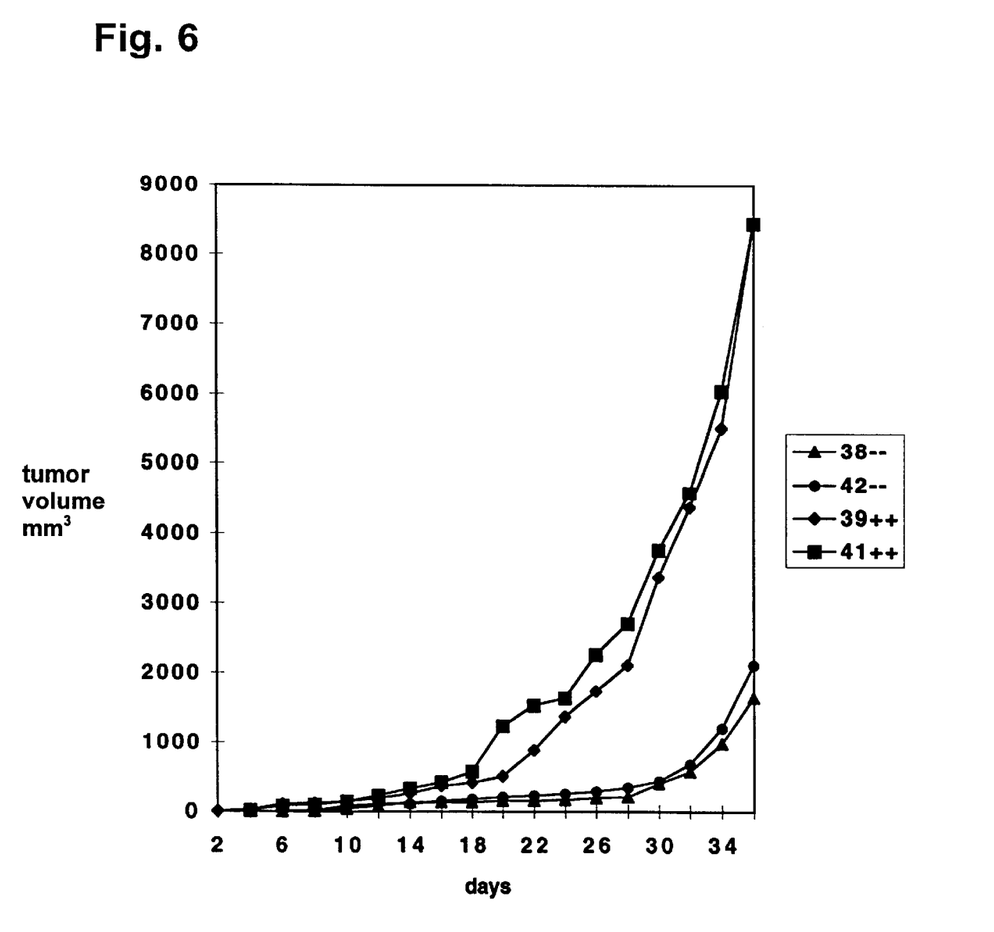
FIG. 6 is a graph comparing the growth of a transplanted tumor in litter-mate homozygous VEGF-B (+/+) and VEGF-B deficient (−/−) mice.

The results are shown graphically in FIG. 6. From the graph it can be seen that the growth of the tumor was significantly slower in the −/− animals compared to +/+ animals. It appears that it is the initial phase, before the exponential growth phase, which is longer in the mutant animals (around 18–20) days for the +/+ animals versus 30–32 days for the −/− animals). This result demonstrates that VEGF-B affects tumor vascularization, probably by affecting the tumor stroma. This conclusion can be drawn since the tumor cells probably express endogenous VEGF-B while the effect is observed in the mutant animals.

The result may be attributable to a direct effect on endothelial cell growth or to an indirect effect such as migration, degradation of extracellular matrix, etc. In either case, the results show that VEGF-B has a role in promoting tumor growth and indicate that anti-tumor strategies can be developed based on inhibition of the action of VEGF-B, for example by blocking the use of monoclonal antibodies to VEGF-B binding to VEGFR-1 or by small molecules binding to VEGFR-1, or by anti VEGF-B therapy, or by a combination of two or more of the foregoing.

The foregoing description and examples have been set forth merely to illustrate the invention and are not intended to be limiting. Since modifications of the disclosed embodiments incorporating the spirit and substance of the invention may occur to persons-skilled in the art, the invention should be construed to include everything within the scope of the appended claims and equivalents thereof.

What is claimed is:

1. A transgenic mouse whose genome comprises a homozygous disruption in the endogenous VEGF-B gene, wherein said disruption in the endogenous VEGF-B gene is caused by the insertion of a DNA sequence into said endogenous VEGF-B gene, and wherein said disruption results in the lack of expression of VEGF-B and wherein said transgenic mice are viable.

2. The transgenic mouse of claim 1, wherein the disrupted VEGF-B gene is disrupted by point mutation, site-directed mutagenesis, deletion, substitution, or insertion.

3. The transgenic mouse of claim 2, wherein the disrupted VEGF-B gene has at least one codon for cysteine changed or deleted.

4. The transgenic mouse of claim 1, wherein the heart of said mouse is smaller than that of a wild-type mouse of the same species.

5. The transgenic mouse of claim 1, wherein the growth of an implanted tumor is slower than the growth of the same tumor in a wild-type mouse of the same species.

6. A method for producing the transgenic mouse of claim 1, comprising:

(a) introducing into a mouse embryonic cell a DNA sequence encoding a selectable marker and having a 5' region and a 3' region of homology to the genomic VEGF-B gene;

(b) selecting an embryonic stem cell from step (a) wherein the DNA sequence encoding a selectable marker has integrated into the genomic DNA of said embryonic cell;

(c) introducing the selected embryonic stem cell from step (b) into a blastocyst of a pseudopregnant mouse, and allowing the blastocyst to develop into a viable transgenic mouse homozygous for a disrupted VEGF-B gene and which results lacks of expression of VEGF-B.

7. The method of claim 6, wherein the disrupted VEGF-B gene comprises a polynucleotide sequence from a VEGF-B gene wherein at least one codon for cysteine has been changed or deleted.

8. The method as claimed in claim 6, wherein the 5' region of homology to the genomic VEGF-B comprises exon 1 of the VEGF-B gene.

9. The method as claimed in claim 6, wherein the 3' region of homology to the genomic VEGF-B comprises exon 7 of the VEGF-B gene.

10. A mouse embryonic stem cell homozygous for a disrupted VEGF-B gene, wherein said disrupted VEGF-B gene comprises a polynucleotide sequence from a VEGF-B gene wherein at least one codon for cysteine has been changed or deleted.

11. A mouse embryonic stem cell homozygous for a disrupted VEGF-B gene, wherein said VEGF-B gene is disrupted by the insertion of a DNA sequence which comprises a 5' region of homology to the genomic VEGF-B comprising exon 1, and a 3' region of homology to the genonic VEGF-B comprising exon 7.

12. The transgenic mouse of claim 1, wherein said DNA sequence comprises a 5' region and a 3' region of homology to the genomic VEGF-B gene.

13. A method for screening a compound for angiogenic or anti-angiogenic activity, said method comprising introducing the compound into a transgenic mouse of claim 1, and assaying the vascular development in the animal.

14. A method for screening a compound for tumor growth modulating activity in a transgenic mouse, said method comprising introducing a tumor cell into a transgenic mouse of claim 1, introducing the compound into the same mouse, and assaying tumor development in the mouse.

* * * * *